United States Patent [19]

Zwick

[11] Patent Number: 4,836,190
[45] Date of Patent: Jun. 6, 1989

[54] VISCERAL RETRACTOR

[76] Inventor: Christian R. Zwick, R.R. 7, Box 46, Quincy, Ill. 62301

[21] Appl. No.: 164,460

[22] Filed: Mar. 4, 1988

[51] Int. Cl.$^4$ ............................................. A61B 17/02
[52] U.S. Cl. ..................................................... 128/20
[58] Field of Search .......................... 128/20, 3, 15, 17; 433/46; 37/120; 56/400.01; 425/118, 221, 276; 16/113, 110 R; 724/20 R, 88; 15/143 R

[56] References Cited

U.S. PATENT DOCUMENTS

| | | | |
|---|---|---|---|
| 2,482,589 | 9/1949 | Maguire | 15/143 R |
| 3,599,621 | 8/1971 | Scrobell | 124/88 |
| 3,901,209 | 8/1975 | Woolsey et al. | 124/20 R |

FOREIGN PATENT DOCUMENTS

| | | | |
|---|---|---|---|
| 1001970 | 10/1951 | France | 16/110 R |
| 2475885 | 8/1981 | France | 128/20 |
| 629923 | 10/1978 | U.S.S.R. | 128/20 |
| 117723 | 8/1918 | United Kingdom | 128/20 |

OTHER PUBLICATIONS

Pilling-Weinberg Vagotomy Retractor-9/63 (advertisement).

*Primary Examiner*—Edward M. Coven
*Assistant Examiner*—Mark S. Graham
*Attorney, Agent, or Firm*—Joseph W. Holloway

[57] ABSTRACT

An arm-actuated surgical retractor according to the invention is tiltable in response to movement of the forearm of an operator by means of a rigid handle extension which arches from the rear of the handle to overlie the forearm above the wrist. The extension may be formed as an abbreviated helix and may be removably mounted on the handle and angularly adjustable with respect to the handle.

7 Claims, 2 Drawing Sheets

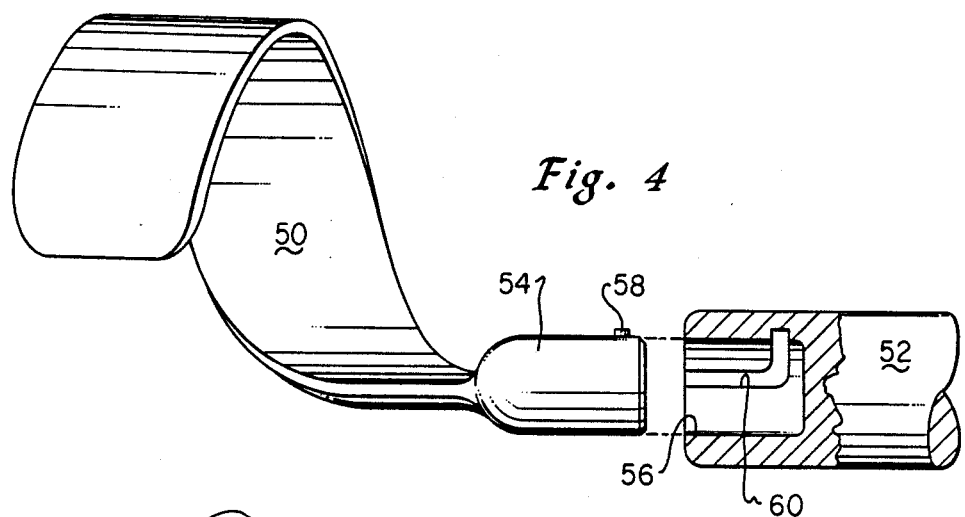
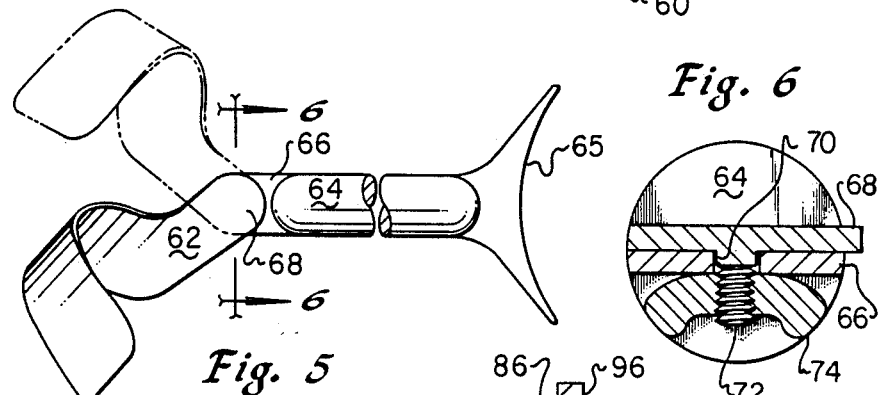
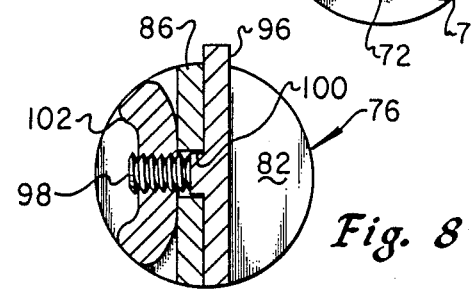
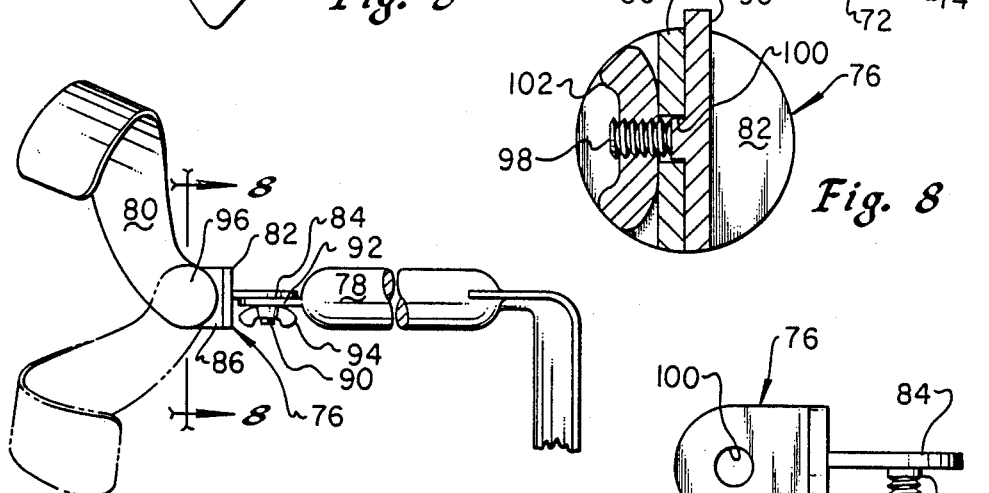
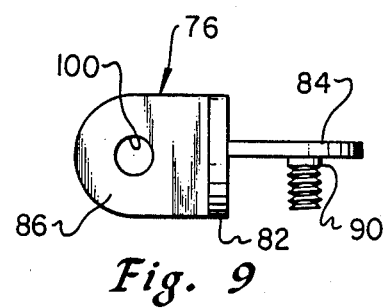

VISCERAL RETRACTOR

BACKGROUND OF THE INVENTION

This invention generally pertains to surgical instruments of the retractor type which are inserted into an abdominal incision and manually manipulated to displace and hold abdominal viscera whereby a surgical field of desired shape and extent is exposed and maintained. More particularly this invention relates to a type of retractor known as a Weinberg retractor being characterized by a broad, deep, metallic blade integrally formed with an elongated handle extending generally perpendicularly to the blade. The size and ruggedness of this class of retractor device are dictated by the need to reach deep into the subdiaphragmatic region to retract tissues and viscera which exhibit substantial weight and inherent resistance to displacement.

While prior art retractors of this class are generally adequate for the intended purpose of establishing an appropriate surgical field, they are not well adapted for continuous retraction during prolonged surgical procedures since the resistance to displacement displayed by the weighty mass of tissues and viscera engaged by the substantial blade surface of the retractor must be continuously overcome by a countervailing force applied to the retractor handle by the muscular effort of a surgical assistant. Therefore, rapid fatigue and acute cramping of the muscle systems of the fingers, hand and wrist are often encountered. Such discomfort may be temporarily alleviated by repositioning the hand with respect to the retractor handle or by replacement of the fatigued hand with the other hand of the operator or with the hand of another operator. However, there exists a substantial risk that the retractor will slip or otherwise release the retracted tissues and viscera back into the surgical field.

The discomfort of a retractor operator is exacerbated where the retractor blade must be continuously pulled toward the operator and simultaneously tilted or toed downwardly and toward the wall of the abdominal cavity in order to maintain a wide surgical field at considerable depth. Such tilting requires that the operator arch or cock his wrist upwardly in order to exert a downthrust and prying action near the lower tip portion of the retractor blade. This maneuver involves application of considerable force by the muscles of the wrist and forearm while adroitly avoiding traumatizing the tissues subjacent the forward end of the retractor handle as the latter is pressed downwardly and pivoted near the margin of the incision. Such careful application of substantial muscular effort is extremely tedious and tiring especially for female surgical assistants.

Another situation which often contributes to rapid operator fatigue arises where the operator cannot comfortably orient his hand and wrist with the retractor handle due to the presence of other medical personnel situated more proximate the surgical field. In this case the operator may be required to reach around or between others in an awkward fashion thereby placing additional strain on the hand and wrist performing the retracting function. Unless suitable manual leverage can be established by lengthening or articulating the handle, steady, prolonged fixation of the retractor blade is nearly impossible.

An alternative visceral retraction method involves the use of a self-retaining device of the wellknown Balfour type. The retractor blade of this type device may be mechanically positioned and held in any desired fixed position. While the fatigue-related problems recited above with respect to manually held retractors are effectively overcome by using a mechanical retractor, the greater flexibility and adaptability of a handheld retractor during the course of many surgical procedures are well understood and appreciated.

Heretofore various handle configurations have been devised to enhance gripping the handle manually. U.S. Pat. No. 659,182 issued Oct. 2, 1900, to C. J. Pilling and U.S. Pat. No. 2,829,649 issued Apr. 8, 1958, to R. J. Glenner are examples of devices provided with handle adaptations intended to provide a more positive manual grasp. However, neither of these prior art retractors recognizes or addresses the problem of operator fatigue since the strain placed on the hand and wrist muscle systems during prolonged usage is not appreciably reduced by the disclosed grip-enhancing features.

SUMMARY OF THE INVENTION

The general object of this invention is to provide a conventional visceral retractor which is structurally modified to obviate the shortcomings of prior art manual retractors presently used for this purpose.

A principal object is to provide an improved retractor of the Weinberg type which is provided with a helically shaped handle extension adapted to overlie and engage the medial region of the forearm of the operator. By this means the muscles of the fingers, hand and wrist which normally operate the retractor are powerfully assisted by the larger muscles groups of the arm and shoulder in applying and maintaining steady retracting force for long intervals. A related object is to lengthen effectively a conventional handle so that the muscle force for tilting the blade against the viscera is applied to the lever-like handle extension at a substantial distance from a fulcrum situated near the marginal edge of the abdominal incision. By utilizing such larger muscle groups to apply force to a longer lever arm the retraction process becomes more efficient and operator discomfort due to strain and fatigue is greatly reduced or eliminated.

Another object is to provide an improved retractor having a helically formed extension integrally attached to a handle grip wherein the extension first projects toward the operator in substantial longitudinal alignment with the grip and then curves upwardly from the grip to extend above and partially around the operator's forearm. In operation, the hand and fingers are utilized solely to grasp the handle grip portion for pulling the blade toward the operator while the lower arm can be raised against the overlying extension to create highly leveraged force for tilting the blade downwardly and outwardly in the desirable manner hereinabove described.

Another object is to provide a helical extension for a retractor which is configured to receive either hand of the operator as desired and which is provided with a substantial surface area which partially surrounds the lower arm and rests in comfortable engagement with the upper surface of the arm during usage.

Still another object is to provide a modified extention which is readily attachable and detachable with respect to the hand grip portion of the retractor to facilitate replacement of wrist levers of different sizes on varying sizes and types of retractors.

Yet another object is to provide in combination a retractor having an extention and means for releasably fixing the extension with respect to the grip portion of the retractor. In a manner hereinafter disclosed, the extension may be angularly adjusted horizontally and vertically to that operator-selected position which provides the greatest comfort for his hand and arm and which allows him to operate the retractor with maximum efficiency regardless of his position relative to the patient and other medical personnel involved in the procedure.

These and other features and objects of this invention and the manner of attaining them will become apparent and the invention will be fully understood by having reference to the following detailed description of embodiments of the invention taken in conjunction with the accompanying drawings.

BRIEF DESCRIPTION OF THE DRAWINGS

FIG. 4 is an elevational and partial sectional view showing an embodiment of the invention in detached relationship with the retractor grip;

FIG. 5 is a top view of an angularly adjustable embodiment of the invention showing the extension in its extreme opposite positions;

FIG. 6 is a section taken along lines 6—6 of FIG. 5;

FIG. 7 is an elevation of another angularly adjustable embodiment of the invention showing the extension in extreme opposite positions;

FIG. 8 is a section taken along lines 8—8 of FIG. 7; and,

FIG. 9 is an enlarged elevational view of an adapter shown in FIG. 7.

DETAILED DESCRIPTION OF THE INVENTION

Figure 1:
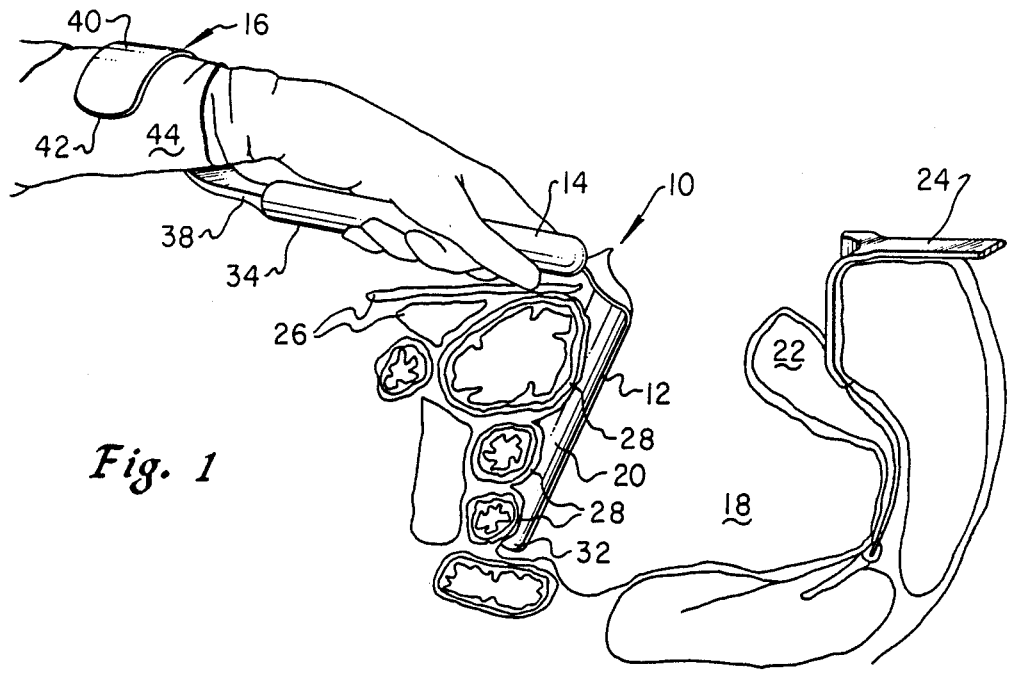
FIG. 1 is a partial sectional view taken through the abdominal cavity showing an embodiment of the invention in use for retracting viscera to expose a suitable surgical field.
Figure 2:
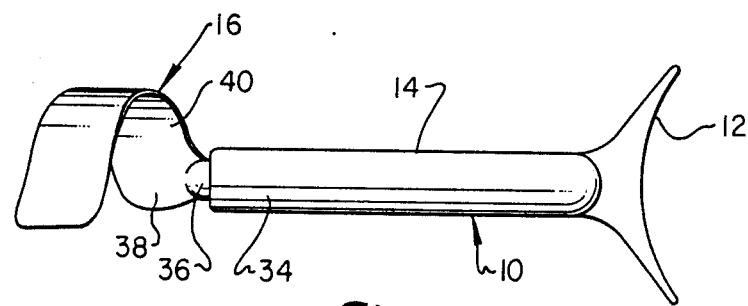
FIG. 2 is a top view of the retractor.
Figure 3:
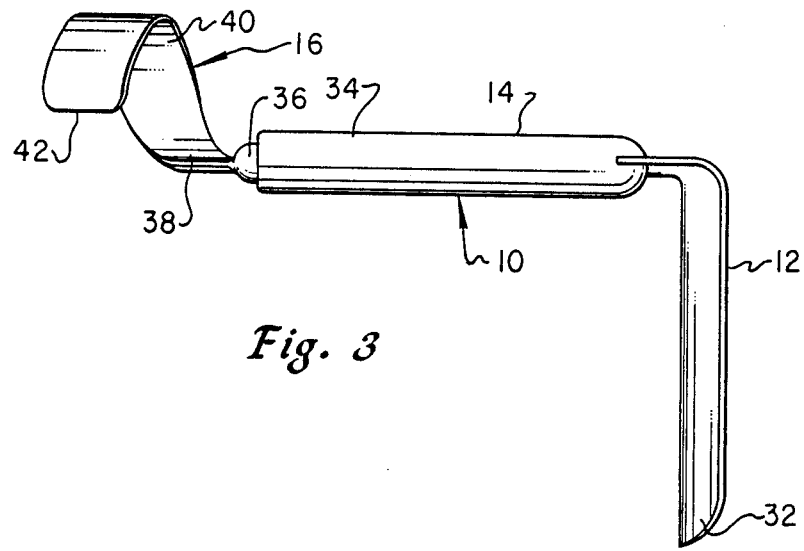
FIG. 3 is an elevational view.

In FIGS. 1, 2 and 3 an improved retractor is designated in its entirety by the numeral 10 and comprises a blade 12, a manual grip or handle 14 and a handle extension 16. The blade and grip are constructed in the manner taught by the Weinberg retractor; however, it will become obvious that the invention may be used to advantage with other types of manual retractors not here illustrated.

As best shown in FIG. 1, the elongated handle 14 is grasped by the operator's hand for inserting the blade 12 downwardly into the abdominal cavity 18. As directed by the surgeon, the operator then engages the convex back surface 20 of the blade 12 against the viscera of the patient and by means of the handle 14 draws the blade and viscera toward the proximate cavity wall with sufficient pulling force to retract the viscera thereby exposing a surgical field which affords access to and visibility of the organ or tissue which is to be surgically treated or removed. In the simplistic illustration at FIG. 1, a gall bladder 22 has been exposed by the retractor 10 in cooperation with the oppositely disposed blades of a retractor of the Balfour type, shown partially at numeral 24. Typically, a cholecystectomy, or gall bladder extraction, requires retraction not only of the abdominal fat and muscle 26 adjacent the incision, but by also of those relatively massive intestinal segments 28 and other organs normally overlying the point of attachment of the gall bladder. This mass of tissue and viscera is not only weighty, but has a natural tendency to resist the substantial displacement required to establish a wide surgical field deep in the abdominal cavity. Not only is considerable operator force required for retraction of this considerable mass, but the retraction force must be maintained during the procedure which, in the case of a cholecystectomy, may last for as long as 2 hours.

Adding to the difficulty of such a deep retraction process is the common requirement that the operator tilt the toe 32 of the blade 12, in the manner shown in FIG. 1, by elevating the rear end 34 of the handle 14 to depress the toe 32 downwardly and toward the side wall of the cavity to displace the viscera 28 disposed adjacent the bottom of the cavity wall. If the operator merely pivots or toes the blade about a fulcrum defined by a point of contact between the forward end of handle 14 and the patient's abdomen, tramatization of the underlying tissue may result. Therefore, in the past, the blade-tilting action has been performed by the operator arching his wrist sharply upwardly while simultaneously drawing the retractor handle toward himself. Rapid and acute fatigue of the finger, hand and wrist muscles is invariably experienced by even the most experienced assistants assigned this task. However, in accordance with the present invention an improved retractor handle is provided with the extension 16 which, as will be described, eliminates the need for the operator to use his wrist to achieve the desired blade toe-in action.

One embodiment of a retractor device, improved in accordance with this invention, is provided with an integral, rigid handle extension 16 shown in FIGS. 1, 2 and 3. The extension comprises an integral shank 36 projecting axially at the extreme rear end 34 of the handle 14 and a flattened tang segment 38 which leads to an open helical segment 40. The helical segment 40 arches upwardly and rearwardly from tang 38 and wraps axially about an axis which is generally parallel with but vertically offset from the longitudinal axis of the handle 14, as will best be understood from viewing FIG. 3. The helical segment 40 wraps about its axis so that its downwardly depending terminal end 42 is disposed substantially rearwardly of the handle 14. The abbreviated helical segment 40 need not completely surround the forearm 44 of an operator, but instead overlies the side of the forearm and transversly spans the upper surface of the same in the manner shown in FIG. 1. The segment 40 slips nicely over the operator's forearm as the handle 14 is grasped by the hand and the forearm 44 passes laterally under and then upwardly to engage the extension. It will be apparent that the helical extension 16 just described will fit in overlying engagement with either forearm depending upon which hand is employed to grasp handle 14 of the retractor 10.

The helical extension 16 is made of the same metal as the handle and blade, stainless steel for example, and has a thickness required to resist deformation during use. Preferably the helical surface 40 has a substantial width thereby providing sufficient surface contact with the operator's forearm to avoid uncomfortable bearing pressure. The rate and rearward extent of axial wrap of helix 40 may be varied as desired from that shown in FIGS. 1, 2 and 3; however, the illustrated configuration suitably accommodates the forearm and hand of male and female operators of average size.

When the improved retractor 10 is employed, the effective lever arm to which blade-tilting force may be applied is considerably lengthened compared to prior art retractors which are not equipped with an extension 16. In response to lifting vertically the forearm 44 subjacent the helical surface 40, an upwardly directed force is applied to the extension 16 which pivots the blade 12 downwardly about a fulcrum generally underlying the operator's fingers which rest on the abdomen of the patient. Not only is this lifting force magnified by the mechanical advantage inherent in a longer lever arm provided by extension 16, but large muscles of the operator's arm and shoulders are employed to generate this force. The concomitant availability of greater muscular force and greater mechanical advantage for tilting the blade downwardly and outwardly against the viscera produces a number of advantages over standard retractors used for the same purpose, namely:

1. The overall efficacy of the retractor is enhanced since increased blade-tilting force is available as needed during various stages of the procedure;

2. The larger muscle groups of the arm and shoulder are not as heavily taxed and therefore are not subject to fatigue to the same extent as the smaller muscles of the fingers, hand and wrist which heretofore provided only marginally effective blade-tilting force;

3. The wrist can be maintained in a natural position without fatigue-inducing arching or cocking; and, 4. The hand and fingers can more efficiently grip and steady the retractor since they are effectively relieved of the blade-tilting task.

An alternative embodiment of the invention illustrated in FIG. 4 contemplates a helical extension 50 which may be removably attached to a handle 52. The extension 50 and handle 52 substantially correspond to the aforedescribed extension 16 and handle 14 except in those structural modifications required to attach and detach these components. Thus a cylindrical shank 54 is received in a cylindrical recess 56 in closely fitting relationship and is locked in recess 56 by the coaction of a conventional type of releasable connector comprising a pin 58 projecting radially from the shank 54 and a J-slot 60 relieved in the side wall of the recess 56. In a well-understood manner, the pin 58 is first aligned with the opening of the slot 60, the shank 54 is then inserted axially into the recess 56 and the shank is finally rotated to seat the pin in the transverse leg of the slot. The utility of a retractor having such a detachable extension 50 is greatly expanded since any combination of interchangeable extensions and retractors may be utilized while retaining the basic advantages of an integral extension. Even during the course of a procedure, the extension 50 may be quickly attached to the handle of any other retractor equipped with an interfitting handle recess whereby the dimensions and configuration of the blade may be selected to meet changing needs. Many types of conventional retractors can be relatively inexpensively upgraded for acceptance of a detachable extension 50 simply by providing an appropriate shank receiving recess and J-slot in the handle.

Another embodiment of the improved retractor, shown in FIGS. 5 and 6, provides for angular articulation of an extension 62 relative to a retractor handle 64. A flat shank 66 projects rearwardly from the end of the handle 64 opposite blade 65 in overlying juxtaposition with a flat tang 68 of a helical extension 62. FIG. 6 shows that the shank 66 has a central aperture 70 which receives therethrough a threaded stud 72 projecting downwardly from tang 68. A threaded fastener 74 which may be of any digitally operable type such as a thumbscrew coacts with the stud 72 for releasably clamping shank 66 and tang 68 in any selected angularly fixed relation between the extreme positions of the extension 62 shown by full and phantom lines, respectively. Thus the extension 62 may be clamped in longitudinal alignment with the handle 64 during normal usage and adjusted, as needed, to extend angularly to either side of the handle's longitudinal centerline. The need for substantial angular articulation of the extension may occur where the operator is unable to position either forearm in suitable alignment with the handle 64 due to the presence of other personnel or equipment thereby making it necessary for him to stand to one side or the other of the requisite line of retraction of the blade 65. Thus, even under circumstances of substantial horizontal misalignment, utilization of the improved extension 62 provides the above-enumerated advantages over conventional retractors.

Still another embodiment of this invention, shown in FIGS. 7, 8 and 9, provides an adapter 76 for a retractor handle 78 which affords substantially universal angular adjustment of an extension 80 with respect to the handle 78. The adapter 76 shown in FIG. 9 has an upright transverse wall 82 from which flat lugs 84 and 86 extend oppositely in planes angularly displaced 90° apart. Lug 84 has a perpendicularly projecting threaded stud 90 which penetrates an aperture through a flat shank 88 formed at the rear of the handle 78 for coaction with a thumbscrew type fastener 94. Similarly, a tang 96 on the extension 80 has a perpendicularly projecting threaded stud 98 which penetrates an aperture 100 through the other lug 86 for coaction with a fastener 102 shown in FIG. 8. With thumbscrews 94 and 102 loosened, the extension 80 may be substantially universally adjusted with respect to the rear end of the retractor handle 76. As viewed in FIG. 7, the extention can be secured by thumbscrew 102 in any vertical position between those shown in full and phantom lines and can be secured by thumbscrew 94 in any horizontal position between the extreme positions described above with respect to extension 62 shown in FIG. 5. It will be understood that the adapter 76 also affords articulated adjustability of extension 80 in the manner described in connection with extension 62 of the FIG. 5 embodiment. Moreover, the adaptor 76 and extension 80 cooperate to provide vertical adjustment of the latter to accommodate extreme variations in the size of an operator's forearm and to compensate for unavoidable vertical misalignment of the operator's forearm with the requisite line of retraction of the retractor blade 104.

The foregoing description of a preferred embodiment of the invention is illustrative and explanatory only and various changes in the size, shape, and materials as well as in specific details of the illustrated construction may be made without departing from the scope and spirit of the invention. For example, the configuration of the extension 16 may deviate from a true helical form so long as some portion of the extension is adapted for bearing engagement with the upper surface of the operator's forearm and the forearm fits comfortably within the extension. While it is necessary that the unitary embodiment shown in FIGS. 1, 2 and 3 be fabricated of a single type of material, the detachable extensions 50, 62 and 80 described herein may be made of materials different from that of the handle and blade with which they are associated should such alternate material provide increased operator comfort, economy in manufacture or other benefits.

What I claim as my invention is:

1. Surgical retractor means tiltable in response to movement of the forearm of an operator, comprising:
   (a) an elongated manually grippable handle;
   (b) a viscera engaging blade affixed to that end of said handle projecting forwardly of the operator's hand;
   (c) rigid handle extension means attached to that end of said handle projecting rearwardly of the operator's hand, said extension means extending rearwardly from said handle sufficiently for engagement with the forearm when said handle is gripped; and,
   (d) said extension means including an open helical portion having a longitudinal axis generally parallel with the longitudinal centerline of said handle and laterally spaced therefrom.

2. The retractor means set forth in claim 1, wherein said extension means is detachably mounted on said handle.

3. The retractor set forth in claim 2, wherein said extension means and said handle are provided with interlocking mounting means.

4. The retractor set forth in claim 3, wherein said mounting means comprise a shank projecting from said extension means into a receiving recess relieved in said handle.

5. The retractor set forth in claim 1, including mounting means for attaching said extension means and said handle in adjustable angular relationship.

6. The retractor set forth in claim 5, wherein said mounting means comprises juxtaposed portions of said extension means and said handle releasably fixed by fastener means.

7. Surgical retractor means tiltable in response to movement of the forearm of an operator, comprising:
   (a) an elongated manually grippable handle;
   (b) viscera engaging means disposed adjacent one end of said handle;
   (c) rigid handle extension means adjacent the other end of said handle and projecting therefrom sufficiently for engagement with the forearm when said handle is gripped;
   (d) mounting means for attaching said extension means and said handle in substantially universally adjustable relationship; and,
   (e) said mounting means comprising a member intermediate said extension means and said handle.

* * * * *